US008649984B2

(12) United States Patent
Nouvelle (10) Patent No.: US 8,649,984 B2
(45) Date of Patent: Feb. 11, 2014

(54) PROCESS AND APPARATUS FOR PROCESSING SIGNALS (75) Inventor: Xavier Nouvelle, Les Matelles (FR)

(73) Assignee: Schlumberger Technology Corporation, Sugar Land, TX (US)

(*) Notice: Subject to any disclaimer, the term of this patent is extended or adjusted under 35 U.S.C. 154(b) by 357 days.

(21) Appl. No.: 13/123,604

(22) PCT Filed: Oct. 16, 2009

(86) PCT No.: PCT/US2009/061031
§ 371 (c)(1),
(2), (4) Date: Apr. 11, 2011

(87) PCT Pub. No.: WO2010/051171
PCT Pub. Date: May 6, 2010

(65) Prior Publication Data
US 2012/0078533 A1 Mar. 29, 2012

(30) Foreign Application Priority Data
Oct. 27, 2008 (FR) ..................... 08 05967

(51) Int. Cl.
G06F 19/00 (2011.01)

(52) U.S. Cl.
USPC ............. 702/27; 702/189; 382/132; 382/232; 382/294; 600/407; 378/62

(58) Field of Classification Search
USPC ............ 702/27, 189; 382/132, 154, 232, 254, 382/294; 600/407; 378/62
See application file for complete search history.

(56) References Cited

U.S. PATENT DOCUMENTS 4,984,160 A * 1/1991 Saint Felix et al. ............. 378/62
2003/0197972 A1 10/2003 Morris
2005/0141757 A1 6/2005 Ayache et al.
2008/0031528 A1* 2/2008 Crombez et al. .............. 382/232
2008/0039706 A1* 2/2008 Chefd'hotel et al. ......... 600/407

FOREIGN PATENT DOCUMENTS

EP 0437829 A1 7/1991
EP 0437829 B1 7/1991

OTHER PUBLICATIONS

Mutihac, Lucia, et al., "Mining in chemometrics,"Analytica Chimica Acta, 2008, pp. 1-18, 612, Elsevier.
Shellie, Robert A., et al., "Statistical methods for comparing comprehensive two-dimensional gas chromatography-time-of-flight mass spectrometry results: Metabolomic analysis of mouse tissue extracts," Journal of Chromatography A., 2005, pp. 83-90, 1086, Elsevier.

(Continued)

Primary Examiner — Carol S Tsai
(74) Attorney, Agent, or Firm — Lam Nguyen; Rodney Warfford; MH2 Technology Law Group (57) ABSTRACT The process of determining similarities of signals resulting from a sample analysis step using the same type of measuring device, characterized by the fact that it comprises a step of determining a value for each parameter of an uncertainty model related to said signals by processing homologous characteristic elements in at least two signals derived from the analysis of similar samples, and a step of determining a measurement of similarity between signals based on each parameter value of the said uncertainty model and of homologous characteristic elements in the different signals whose similarity is being measured. In some embodiments, during the value determination step, a mathematical uncertainty model is optimized so that it corresponds to the theoretically expected differences between the homologous characteristic elements in the various signals from similar samples.

21 Claims, 4 Drawing Sheets (56) References Cited

OTHER PUBLICATIONS

Hu, Yuzhu, et al., "Assessment of chromatographic peak purity by means of artifical neural networks," Journal of Chromatography A., 1996, pp. 259-270, 734, Elsevier.

Malmquist, Gunnar, et al., "Alignment of chromatographic profiles for principal component analysis: a prerequisite for fingerprinting methods," Journal of Chromatography A., 1994, pp. 71-88, 687, Elsevier.

* cited by examiner

PROCESS AND APPARATUS FOR PROCESSING SIGNALS

This invention concerns a process and an apparatus for processing signals. It applies in particular to the processing of signals representative of the measurements made on samples in order to determine similarities between them. More specifically, this invention applies to the signals generated by a chromatograph in order to determine whether two samples of oil come from reservoirs or horizons that are connected.

The characterization of reservoir continuity provides information aimed at reducing the key uncertainties in an oil field whose exploitation is being contemplated, and at planning and implementing optimum reservoir development. Such characterization is therefore of great interest to the oil industry.

Reservoir characterization and reservoir continuity studies can be achieved in various ways. Some examples of characterization methods aimed at estimating reservoir compartmentalization are PVT (Pressure, Volume, Temperature) measurements, isotope analysis, GCMS (Gas Chromatography—Mass Spectrometry) techniques or FTIR (Fourier Transform Infra Red) spectroscopy, and multidimensional gas chromatography.

Among these methods, the use of oil fingerprints obtained by the analysis of gas chromatograms of crude oil is one of the quickest and least expensive.

The oil fingerprint technique is relatively simple to implement. It consists of comparing various gas chromatograms of samples from different wells in an oil field. The differences between the chromatograms are used as indicators to identify possible barriers between the reservoirs covered by these wells.

Since the beginning of the 1980's, this technique, called ROF (Reservoir Oil Fingerprinting), has been widely used to estimate the connections between reservoirs or, what amounts to the same thing, the presence of flow barriers between two reservoirs. The ROF method is based on the comparison of several chromatograms obtained in the same chromatographic conditions. More specifically, it is based on the differences between the peak height ratios of the various samples analyzed.

The two peak heights used to calculate each ratio are generally selected so that they are close to one another in order to avoid differences due to phenomena other than reservoir compartmentalization, such as evaporation, gravitational gradients, and the immobilization of heavy components in the chromatograph. In effect, the incoherencies introduced by these mechanisms are particularly significant for components having significant retention time differences.

It is generally accepted that the accuracy of chromatographic analysis is on the order of 1 to 3%. Based on that range, differences in peak height ratios of 5 to 10% or even more cannot be attributed to analytical errors and should represent real differences in crude oil composition. It is therefore customary to use a restricted selection of the most discriminating ratios in order to separate crude oils into meaningful groups. These groups can then be represented on star diagrams that represent the ratios in one plane in order to facilitate comparison.

However, this technique presents serious limitations, particularly with respect to the uncertainties as to peak height ratios: the repeatability deviations of the analysis conditions and the deterioration of the chromatographic column over time play a decisive role that is not taken into account. Furthermore, the uncertainty as to each ratio is highly dependent upon the chromatographic peaks used in this ratio. Problems such as coelutions (simultaneous detection of different components poorly separated by chromatography) or measurement noise result in specificity of the error assigned to each ratio. This problem can lead to erroneous interpretations of the chromatographic data. As proof of this, changing the list of the peak height ratios to be used in a star diagram can lead to very different results.

In addition, since only a restricted number of peak height ratios is considered, the star diagram is only a partial representation of the spatial topology of all of the peak height ratios. Furthermore, slight but numerous differences in composition between samples can have a considerable impact. This compositional variability and the subsequent difficulty of restricting the number of peak height ratios selected can lead to erroneous results.

Other interpretations using GC (Gas Chromatography) peak height ratios in statistical methods are also possible, such as ascending hierarchical classification, main component analysis, or fuzzy logic classification.

However, it is important to note that all these methods are based on relative differences in peak height ratios, the uncertainty of which is undetermined. The results obtained are therefore not expressed in absolute terms and are restricted to the comparison of crude oil samples on a scale that is never the same from one series of comparisons to another.

In other words, the current state of the art does not provide a scale on which differences between samples can be universally measured. The experience acquired on past projects is therefore of little use for future projects. This is all the more annoying because there may be slight differences in composition within a single reservoir or reservoirs that are after all connected (phenomenon of compositional gradients). In the current state, since the amplitude of these phenomena cannot be universally quantified, specialists cannot determine whether differences between samples do or do not signify actual permeability barriers between reservoirs.

This invention is aimed at remedying these disadvantages.

To that end, this invention is first aimed at a process of determining similarities between signals from a sample analysis step using a single type of measurement apparatus, characterized in that it comprises:

a step of determining a value for each parameter of an uncertainty model related to said signals by processing homologous characteristic elements in at least two signals derived from the analysis of similar samples, and a step of determining a similarity measurement between signals based on each parameter value of the said uncertainty model and of homologous characteristic elements in the signals whose similarity is being measured.

The term "homologous" refers to signals that are characteristic of a specific measurement present in the various analyses, i.e., peaks of a given compound in different signals (in the specific case of chromatography, the peaks of a given compound present in different chromatograms).

As a result of these methods, the similarity measurement is directly related to the uncertainty of the measurements. It is observed that the higher the number of peak height ratios associated with the signals, the more precise the determination of the values of the uncertainty model and the more accurate the similarity measurement. Note here that the similar samples do not necessarily come from a single initial sample: the same sample may merely be analyzed twice, or two samples may be independently taken from the same reservoir and then analyzed.

In some embodiments, during the value determination step, a mathematical uncertainty model is optimized so that it corresponds to the theoretically expected differences between the homologous characteristic elements in the signals from similar samples.

In some embodiments, during the value determination step, a mathematical uncertainty model is optimized so that the distribution of the Student variables constructed from the said model corresponds to a theoretical Student distribution with one degree of freedom of the differences between the homologous characteristic elements in the signals from similar samples.

In some embodiments, during the parameter value determination step, the parameter values minimize the quadratic distance between a theoretical cumulative distribution function and the cumulative distribution function obtained with the characteristic elements of a pair of signals from similar samples.

In some embodiments, during the similarity measurement determination step, the mean difference is determined between the distribution obtained by calculating the differences between the homologous characteristic elements in the signals whose similarity measurement is being determined and a theoretical distribution based on the said parameter values.

In some embodiments, during the similarity measurement determination stage, the mean difference is determined between the distribution obtained by calculating the differences between the homologous characteristic elements in the signals whose similarity measurement is being determined and a theoretical Student distribution based the said parameter values.

In some embodiments, during the similarity measurement determination stage, the mean difference is determined between the distribution obtained by calculating the difference between the homologous characteristic elements in the signals whose similarity measurement is being determined and a theoretical Gaussian distribution based on the said parameter values.

In some embodiments, during the similarity measurement determination stage, a deviation between the samples is supplied based on the said mean difference.

It is observed that this deviation is independent of the number N of accessible ratios and independent of the sample analysis system, that this deviation is global and absolute (the deviation being independent of the sample analysis system). This deviation makes it possible to create case study databases directly usable for comparisons with any new study project or any new sample analysis apparatus. In effect, since the deviations between the samples are expressed on an absolute scale, the knowledge acquired at one site can be utilized for subsequent studies. For example, for an application to an oil field exploitation project, these databases make it possible in particular to establish composition (or similarity) variation thresholds after which a barrier can be considered to exist between the reservoirs that supplied the crude oil samples.

In some embodiments, during at least one determination step, the homologous characteristic elements are peak heights present in the different signals. It is observed that this implementation method is preferentially suited to the use of a Gaussian distribution.

In some embodiments, during at least one determination step, the homologous characteristic elements are peak height ratios present in the different signals.

It is observed that this embodiment is preferentially suited to the use of a Student distribution.

In some embodiments, during the analysis step, a gas chromatograph is used to supply chromatogram signals.

It is therefore possible to determine the similarities between samples that can be analyzed with such a chromatograph, such as samples of crude oil.

In some embodiments, during at least one determination step, an uncertainty model described by the following equation is used:

$$(\sigma_{Hi}^{Th})^2 = (\alpha \cdot Hi + \beta)^2$$

in which $\alpha$ and $\beta$ are parameters to be optimized and $H_i$ is the normalized height of peak i.

The inventor has in fact determined that such an uncertainty model does correspond to numerous sample analyses, such as chromatographic analyses.

Second, this invention is aimed at an apparatus for determining similarities of signals from a sample analysis step using a single type of measurement apparatus, characterized in that it comprises:

a means of determining a value for each parameter of an uncertainty model related to the said signals by processing homologous characteristic elements in at least two signals from the analysis of similar samples, and a means of determining a similarity measurement between signals based on each parameter value of the said uncertainty model and homologous characteristic elements in the signals whose similarity measurement is being determined.

Since the advantages, objectives, and special characteristics of this apparatus are similar to those of the process according to this invention, as briefly explained above, they are not described herein.

Other advantages, objectives, and special characteristics of this invention will become apparent from the following description, which is for explanatory purposes and in no way limits the attached drawings, in which.

As explained above, this invention concerns, in general, a process and an apparatus for processing signals. It applies in particular to the processing of signals representative of measurements made on samples in order to determine similarities between them, as explained in relation to FIG. 1. More specifically, this invention applies to signals generated by a chromatograph in order to determine whether two samples of oil come from reservoirs or horizons that are connected, as explained in relation to FIG. 2.

Figure 1:
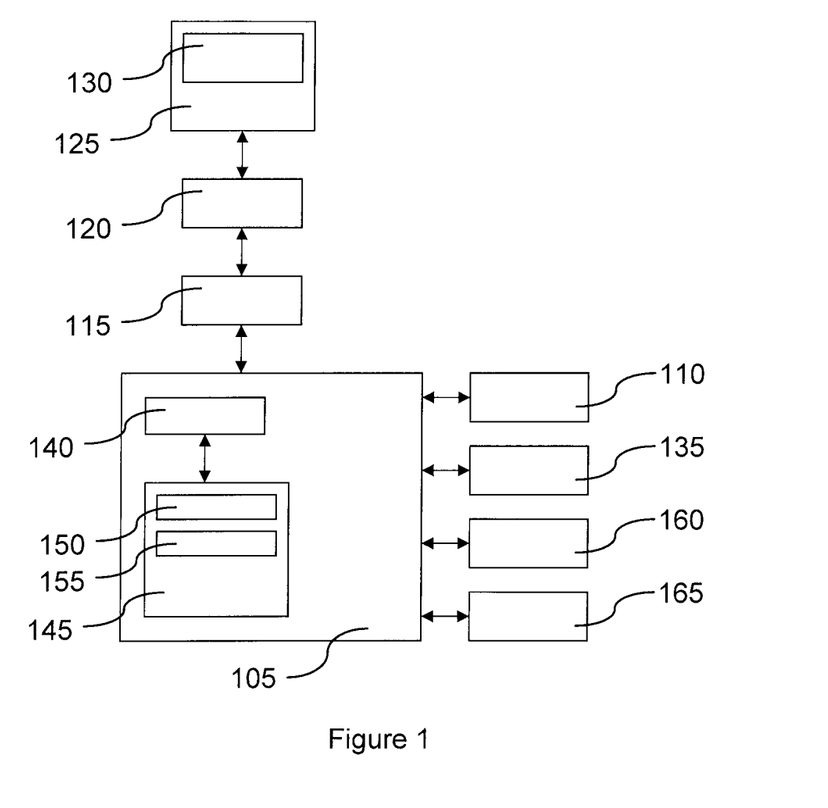
FIG. 1 schematically represents a first implementation method of a device according to this invention, FIG. 2 schematically represents an oil field with wells, FIG. 3 schematically represents extracts from gas chromatograms of samples of crude oil.

FIG. 1 shows a local terminal 105 equipped with a printer 110, a means of capturing physical quantities 135, and a means of access 115 to a network 120 to which a server 125 is connected. The server 125 is furnished with a database 130.

The local terminal 105 is, for example, a commonly used computer. The local terminal 105 commands the printing of sample similarity tables and the interpretation of such tables. The means of access 115 to the network 120 is, for example, a modem of a known type permitting access to the network 120, for example the internet.

The server 125 is of a known type. The database 130 contains at least a list of similarity or deviation measurements between samples already processed using the process according to this invention, along with sample identifiers and possibly means of capturing physical quantities 135 used to analyze the said samples.

The terminal 105 contains software which, when run, implements the steps in the process according to this invention. The server 125 contains software which, when run, implements the steps of a similarity or deviation measurement storage and access process.

Alternatively, the terminal 105 does not contain specific software but implements a web browser and a web service contained in the server 125.

The terminal 105 and/or the server 125 is adapted to determining similarities in signals from the same means of capture 135, also called "measuring device." To that end, the terminal 105 and/or the server 125 contains:

a means of determining a value for each parameter of an uncertainty model related to the said signals by processing homologous characteristic elements in at least two signals from the analysis of similar samples, and a means of determining a similarity measurement between signals based on each parameter value of the said uncertainty model and homologous characteristic elements in the signals whose similarity measurement is being determined.

These means are, for example, composed of a microprocessor 140 and memories 145 containing an operating system 150 and application software 155 containing instructions to implement the process according to this invention.

Lastly, in a known manner, the local terminal 105 is equipped with a display screen 160 and means of control 165, for example a keyboard and a mouse.

The following describes an implementation of this invention for processing signals from a means of capture 135 composed of a gas chromatograph adapted to produce chromatograms of crude oil samples. However, this invention is not limited to this type of means of capture, but on the contrary extends to all types of means of capturing physical quantities, such as sound, mechanical, electrical, or magnetic signals, vibrations, or images. It makes it possible to determine a level of similarities between signals from such means of capture. For example, this invention can be used to recognize or differentiate voices, pronounced words and phrases, objects present in visual or audio scenes, seismic shocks, and electromagnetic waves.

In the case of application to the oil industry, this invention uses a new statistical method for analyzing gas chromatograms, which is based on a coherent quantification of the uncertainty of peak height measurements. The quantification of the uncertainties inherent to each peak height permits a more precise differentiation. Note that it may be used in other fields, such as commingled streams allocation.

Figure 2:
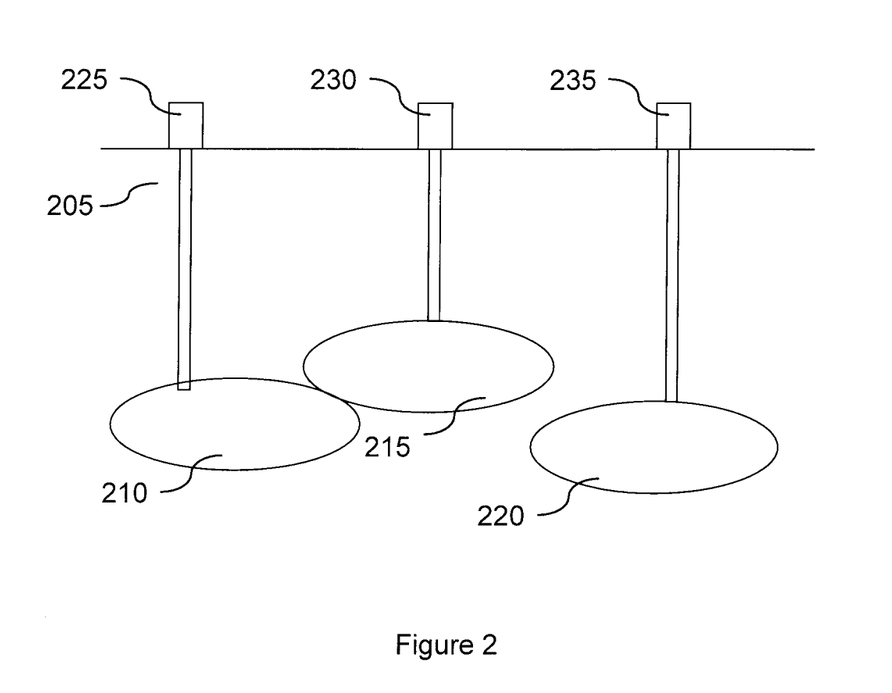

FIG. 2 shows underground crude oil reservoirs 210, 215, and 220 in an oil field 205. Sample collection wells 225, 230, and 235 permit the collection of samples in each of the reservoirs 210, 215, and 220, respectively.

One of the problems posed for the exploitation of this oil field is the number of wells necessary to reach all the reservoirs. Correlatively, there is an effort to find reservoirs that are connected by an oil flow such as reservoirs 210 and 215 in FIG. 2, and reservoirs that are not connected, for example reservoir 220 is not connected to reservoir 210 or to reservoir 215. The processing of gas chromatograms using the process according to this invention makes it possible to estimate a similarity of the chemical compositions of the crude oil samples collected and, accordingly, to provide a probability of connection between reservoirs.

Figure 3:
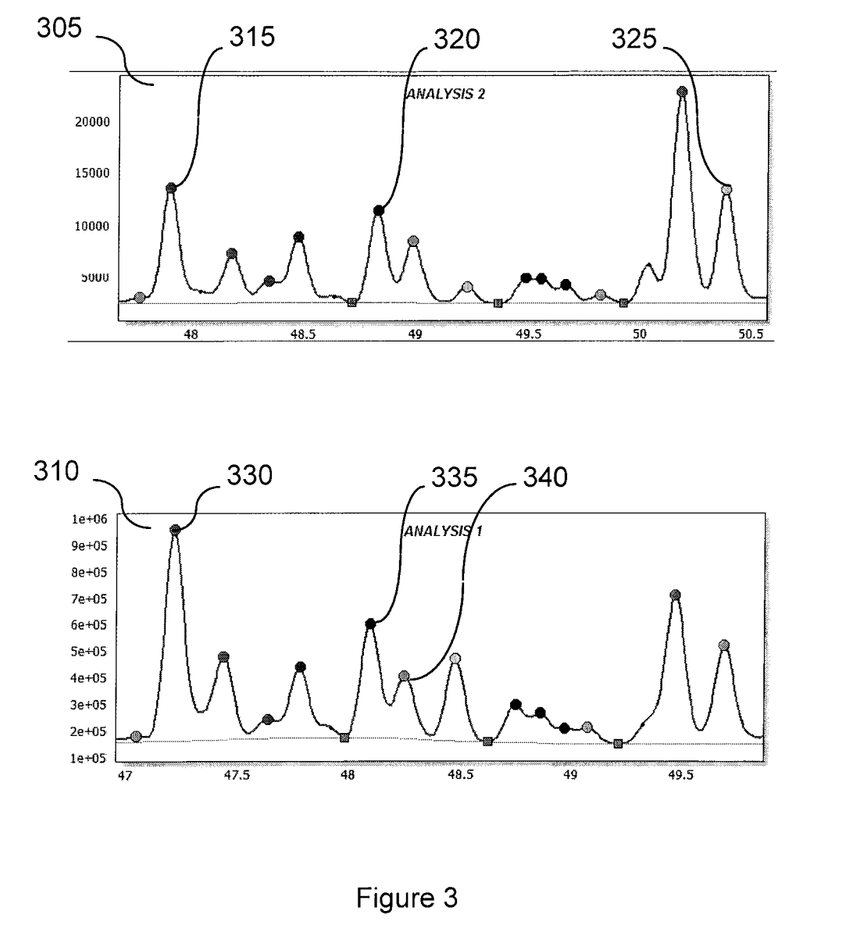

Two chromatogram extracts 305 and 310 illustrated in FIG. 3 show that each chromatogram extract contains peaks, 315 to 325, and 330 to 340. respectively. These peaks may be facing each other on the two chromatograms, like peaks 315 and 330. They may also be very close on the same chromatogram, like peaks 335 and 340. If the height of one peak influences the height of the other, there is coelution.

In the remaining of the description, the peak height ratios of each chromatogram are considered that chromatogram's footprint. Note that as many peaks as possible, even all the peaks, are used. These peaks are common to all the chromatograms, i.e., the peaks have the same Kovats index to within one chromatographic peak width.

It should be noted here that Kovats indices are relative retention values calculated so as to be independent, to the first order, of the chromatographic conditions in which the samples were analyzed. The Kovats index of a compound i is calculated using the following equation:

$$\text{KovatsID}(i) = 100 \cdot (nC_{i-1} + (\log_{10}(t_i) - \log 10(t_{Ci-1})) / (\log_{10}(t_{Ci}) - \log 10(t_{Ci-1}))$$

where:

KovatsID(i)=Kovats index of compound i, $n_{Ci-1}$=Number of carbons of the n-paraffin located just before compound i, $t_i$=Retention time of compound i, $t_{Ci-1}$=Retention time of the n-paraffin located just before compound i, and $t_{Ci}$=Retention time of the n-paraffin located just after compound i.

Figure 4:
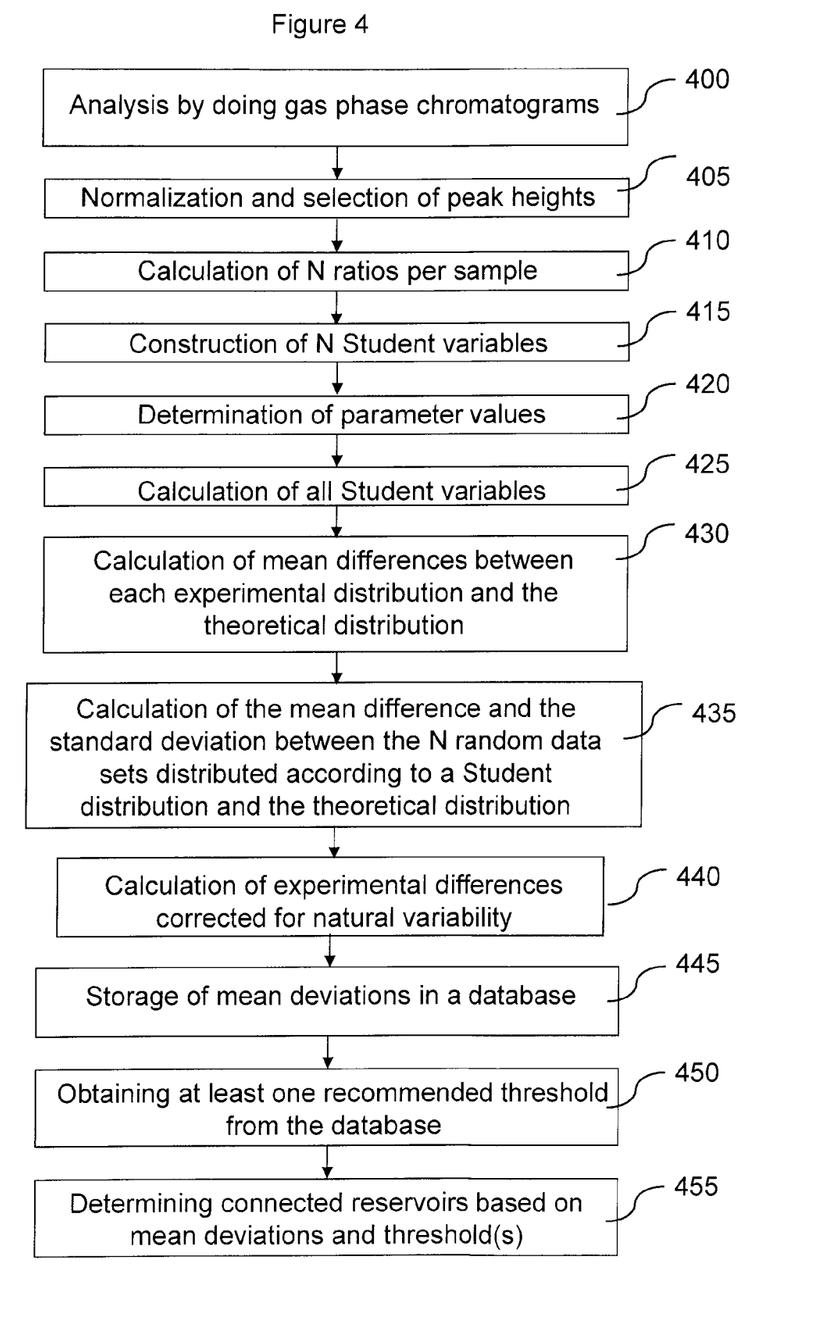
FIG. 4 represents, in the form of a logic diagram, the steps taken in a specific embodiment of the process according to this invention.

As can be seen in FIG. 4, in a specific embodiment, the first step 400 of the process consists of making a chromatogram for each sample collected, and identifying the chromatograms that involve samples from the same sample collection well.

Then, in a step 405, the peaks of the signals representing the chromatograms are normalized so as to offset the differences in injected volume of the samples in the chromatograph system, as expressed below with respect to Equation (4). In this same step 405, the homologous peaks from all the chromatograms are selected, i.e., those having the same Kovats index. This provides characteristic measurements specific to each sample in the form of the selected peak heights.

In a step 410, N ratios of these characteristic measurements are calculated for each sample.

In a step 415, N Student variables are constructed from the N ratios of each pair of samples and from an uncertainty model whose parameters are to be optimized.

In a step 420, from the pairs of analyses assumed to be similar and from the Student variables, the values of the parameters that optimize the uncertainty model are determined.

In a step 425, all the Student variables for all the other pairs of analyses are calculated using the parameters optimized in step 420.

In a step 430, for each pair of analyses, the mean difference between the distribution of the N Student variables and a theoretical Student distribution with one degree of freedom is calculated.

In a step 435, the mean deviation is established between sets of N random data distributed according to a Student distribution and a theoretical Student distribution. The standard deviation is also calculated. These values represent the expected natural variability for N variables.

In a step 440, the mean deviation determined in step 435 is subtracted from the mean difference determined in step 430 so as to define a zero difference when two analyses are similar. The uncertainty as to the mean difference between two analyses is also given by the standard deviation determined in step 435.

With respect to steps 415 and 420, a mathematical model is constructed in order to estimate the uncertainties as to the peak height ratios between two chromatograms using the pairs of analyses pertaining to the same crude oil sample(s) and using the theoretical distribution of the expected errors (in the case of peak height ratios: Student distribution with one degree of freedom).

The uncertainty model must meet two criteria: it must be sufficiently flexible so that the distribution of the Student variables (constructed from the uncertainty model) is in keeping with the Student distribution with one degree of freedom, but is at the same time sufficiently general to apply to a series of analyses relatively close to one another in time. Numerous tests were conducted in order to find the best compromise between these two criteria.

With respect to the model distribution curve (Student distribution with one degree of freedom), it can be shown that the variables constructed from Equation (2) below are distributed according to a Student law with one degree of freedom. In this case, this model curve is therefore fixed once and for all. However, the technique used could also be applied to more conventional measurements having a Gaussian type error, for example using peak heights instead of peak height ratios. In this case, since the variables are not in the form of ratios, it is simply necessary to use the normal law instead of the Student law with one degree of freedom.

The number of analyses to be done successively on a single batch, i.e., a single series of analyses with the same means of capture, in this case the same chromatograph, is restricted for two main reasons. First, the chromatographic analysis of crude oil takes time. In addition, chromatographic data are increasingly altered as more analyses are done with the same chromatographic column.

Since the number of measurements of the height of the same peak of the same fluid is very limited, the common uncertainty calculations, such as standard deviation, cannot be done with precision.

For the implementation of the process according to this invention, the numerous peak height ratio measurements in each chromatogram are used. The Student variable t is used, which is expressed as:

$$t = \frac{(\bar{x} - \mu)}{\sigma_e / \sqrt{n}} \quad (1)$$

in which:

$\bar{x}$ is the mean value of the sample for a descriptive variable x, $\mu$ is the expectation for variable x, $\sigma_e$ is the standard deviation estimator for the population, and n is the number of independent measurements in the sample.

In our case, the variables are the peak height ratios.

For two chromatograms representing the same crude oil, the expectation $\mu$ is zero for each variable. In such a configuration, the Student variable t associated with each peak height ratio can be written:

$$t_{ij} = \frac{\left(\left(\frac{H_i}{H_j}\right)_{Chromato.1} - \left(\frac{H_i}{H_j}\right)_{Chromato.2}\right)}{\sqrt{\left(\sigma_{H_i/H_j}\right)^2_{Chromato.1} + \left(\sigma_{H_i/H_j}\right)^2_{Chromato.2}}} \quad (2)$$

where $H_i$ is the normalized height of peak i.

The distribution of such a variable is known as Student distribution with one degree of freedom. When the number of variables $t_{ij}$ for each chromatogram is reasonably high, the theoretical distribution of such variables is approached if the denominator in Equation (2) is correctly estimated.

Four error factors can be determined in the measurements in the chromatograms:

The first concerns the peak height in the measurement, where it can be considered that the lower the peak, the higher the relative error;

The second refers to the phenomenon of coelution, which has a direct effect on peak height; the greater the coelution, the more a peak is modified by the contribution of neighboring peaks; the ratio between the peak heights and the height of its highest valley gives a good representation of the degree of coelution;

The third concerns the difference between the retention times of a given compound in successive analyses; in effect, if the retention time of a given compound varies from one analysis to another, the peak height measurements may be estimated erroneously due to the phenomenon of coelution, the positioning of the baseline, or erroneous identifications;

The last factor involves the height of the baseline: the higher the baseline, the greater the uncertainties on the peak height measurement. All these factors were integrated in conceptual models. Each of these models was tested with different sets of data in order to determine its accuracy and its strength.

In order to optimize the conceptual model, since a pair of chromatograms comes from the same crude oil sample, the cumulative distribution function, or CDF, of the t variables on each peak height ratio should follow the same trend as the theoretical t-Student distribution with one degree of freedom.

These considerations were used to optimize the models: their optimum values are the values that minimize the quadratic distance between the theoretical CDF and the experimental CDF obtained with pairs of chromatograms from the same sample of crude oil.

The best uncertainty model is therefore the one that minimizes this criterion, but also the one that has the best potential of being universal. This latter requirement is evaluated by splitting the pairs of chromatograms of the same samples of crude oil into two groups: the first is used to optimize the parameters of the model and the second is used to validate its universality. Universality means that the validation data (pairs of samples not used for the optimization of the uncertainty model but acknowledged to be similar) must exhibit a similarity comparable to that found for the data used for optimization. If this is not the case, the uncertainty cannot be used, for example due to an excessively rapid change in the measurement system. It is therefore recommended that the same sample be analyzed at the end of the series of samples as at the beginning. Alternatively, the parameter values determined at various stages of the series of samples analyzed are interpolated.

The various simulations lead to the reduction of the number of variables in the uncertainty estimate and the best conceptual model can be described by the following equation:

$$(\sigma_{Hi}^{Th})^2 = (\alpha \cdot Hi + \beta)^2 \quad (3)$$

in which α and β are parameters to be optimized and is the normalized height of peak i.

The peak heights are normalized in order to avoid potential effects of scale, using the following formula:

$$(H_i^{Fluide\ 1})_{Norm} = \frac{H_i^{Fluide\ 1}}{\left(\frac{1}{N_H}\sum_{j}^{N_H} H_j^{Fluide\ 1}\right)} \quad (4)$$

In effect, as illustrated in FIG. 3, peak amplitude may vary considerably from one fluid to another without increasing the relative uncertainty.

The calculation of the propagation of uncertainties can then be expressed as $$\sigma_{Hi/Hj}^{Th} = \frac{1}{H_j}\sqrt{(\alpha \cdot H_i + \beta)^2 + \left(\frac{H_i}{H_j}\right)^2(\alpha \cdot H_j + \beta)^2} \quad (5)$$

which permits the transposition of the peak height uncertainties to peak height ratios.

The distributions of the experimental (Equation 2) and theoretical Student variables are then compared in order to obtain an absolute measurement of the differences between the footprints composed of the chromatogram peak height ratios.

It is known that the characterization of the barriers between oil reservoirs is often complicated by the variability of the fluid composition in a given reservoir. Since the conventional method used to characterize compartmentalization is applied on a relative scale, and with a restriction of the peak height ratios, the composition variability due to true compartmentalization or due to thermo-gravitational (or other) effects cannot be quantified.

In order to solve this critical problem, the inventor has calculated an absolute deviation between the samples of crude oil. From one case to another, since the deviations are expressed on a comparable scale, the exact involvement of flow barriers and internal reservoir variability can be quantified and therefore taken into account. However, since the uncertainties on peak height ratios are not the same from one series of analyses to the next, the inventor has opted to use the Student t variable distribution curves obtained for each pair of fluids. Since each analysis is transposed in terms of t-variables, and since these variables are independent of the amplitude of the uncertainties, the mean deviation between the theoretical and experimental CDF values is expressed on a universal scale. Using the natural variability of N random variables (N being the number of peak height ratios used) distributed according to a Student distribution with one degree of freedom, the uncertainty on the evaluation of difference can also be estimated.

The simplest way to evaluate the mean deviation between the theoretical and experimental CDF values consists of applying the following formula:

$$D_{Fluide1/Fluide2} = \frac{1}{N}\sqrt{\sum_{i=1}^{n}(CDF_{Fluide1/Fluide2}(t_i) - CDF_{Theo}(t_i))^2} \quad (6)$$

in which:

$CDF_{Fluide1}/Fluide_2(t_i)$ is the CDF associated with each experimental variable $t_i$ $CDF_{Theo}(t_i)$ is the CDF associated with the same theoretical variable $t_i$, and N is the number of t-variables.

However, this method is not sufficient when some experimental CDF values are narrower than the theoretical CDF. In such cases, the calculated deviation between the CDF values would be large, while any single-point comparison of the pair of chromatograms would be closer than expected.

This situation appears when the pairs of chromatograms used to establish the uncertainty model are less distant than others that were not used. This may occur because the CDF comparison method is sensitive enough to register the gradual deterioration of the chromatograph columns during the cycle of analyses of a set of crude oil samples.

The mean deviation between the experimental and theoretical CDF values is finally calculated using the following formula:

$$D_{Fluide1/Fluide2} = \frac{1}{n}\sum_{i=1}^{n} d_i \quad (7)$$

The values of the $d_i$ depend on the values of the variables ti:

$$si\ t_i<0:\ d_i=CDF_{Exp}(t_i)-CDF_{Theo}(t_i) \quad (8)$$

$$si\ t_i>0:\ d_i=CDF_{Theo}(t_i)-CDF_{Exp}(t_i) \quad (9)$$

This result avoids penalizing experimental distributions that are narrower than expected according to the uncertainty model: such a case would be represented by a negative difference.

With respect to the expression of the uncertainty on the various calculations, a generator of random variables distributed according to a Student distribution with one degree of freedom was constructed. It can be used to do a simulated CDF with N random variables to calculate its differences from the theoretical CDF according to Equations (7), (8), and (9).

This process can also be repeated hundreds of times in order to estimate its standard deviation. This latter value corresponds to the natural variability of simulations of N variables. If the number of random variables N coincides with the number of independent ratios of the set of real data, it can be used as a reliable estimate of the uncertainty on the difference between experimental and theoretical CDF values.

In a step 445, the deviations between the footprints are stored on an absolute scale in a database. Which permits the creation of case study databases directly usable for comparisons with any new study project. In effect, since the deviations between samples are expressed on an absolute scale, the knowledge acquired on a series of analyses can be utilized for subsequent studies.

Among other things, these databases make it possible to establish composition variation thresholds beyond which a barrier can be considered to exist between the reservoirs that supplied the oil samples.

In a step 450, recommended deviation thresholds can be recovered from the database beyond which samples are considered as not coming from interconnected reservoirs.

In a step 455, on the basis of the recommended thresholds or thresholds specifically determined for the project, samples that come from reservoirs that are probably interconnected can be estimated based on the deviations between samples.

Table 1 below concerns two data sets consisting of several sample analyses. Each data set contains analyses of fluids from different wells but from the same oil field.

Some samples were analyzed twice in order to construct the uncertainty model on each data set and in order to validate it.

In Table 1, the order in which the analyses were made has been preserved. This can be important because the quality of the peak height measurements can deteriorate as the analyses progress. For each data set, the uncertainty model was constructed with the first sample.

TABLE 1

| Analysis | Sample |
|---|---|
| Data set 1 | |
| A1 | 1 |
| B1 | 2 |
| C1 | 3 |
| D | 4 |
| E | 5 |
| F | 6 |
| G | 7 |
| C2 | 3 |
| B2 | 2 |
| A2 | 1 |
| Data set 2 | |
| A1 | 1 |
| B1 | 2 |
| C1 | 3 |
| D1 | 4 |
| D2 | 4 |
| C2 | 3 |
| B2 | 2 |
| A2 | 1 |

The following describes an example of implementation of the process according to this invention. In this example, only sample 1 (analyses A1 and A2) was used to obtain the uncertainty model for each data set. The result is given in Table 2 below:

|    | A1     | A2    | B1     | B2    | C1     | C2    | D     | E     | F      |
|----|--------|-------|--------|-------|--------|-------|-------|-------|--------|
| A2 | −0.002 |       |        |       |        |       |       |       |        |
| B1 | 0.198  | 0.195 |        |       |        |       |       |       |        |
| B2 | 0.196  | 0.194 | −0.023 |       |        |       |       |       |        |
| C1 | 0.182  | 0.181 | 0.156  | 0.157 |        |       |       |       |        |
| C2 | 0.180  | 0.180 | 0.159  | 0.161 | −0.015 |       |       |       |        |
| D  | 0.190  | 0.189 | 0.145  | 0.151 | 0.073  | 0.093 |       |       |        |
| E  | 0.198  | 0.197 | 0.087  | 0.099 | 0.157  | 0.160 | 0.146 |       |        |
| F  | 0.192  | 0.191 | 0.062  | 0.063 | 0.156  | 0.157 | 0.145 | 0.087 |        |
| G  | 0.196  | 0.193 | 0.049  | 0.059 | 0.154  | 0.157 | 0.142 | 0.056 | −0.002 |

Analyses B1 and B2 (sample 2) and analyses C1 and C2 (sample 3) validate the uncertainty model because they are not used to construct it. The analyses of these two pairs are narrower than expected, since their difference with respect to theory is slightly negative (−0.023 and −0.015, respectively). This can be explained by the order in which the analyses were done. Analyses F and G cannot be differentiated either (result of −0.002). This result means that samples F and G come from reservoirs that are connected, or from separated reservoirs in which the crude oil has the same chemical composition (also called "false negatives").

The other analyses show significant differences in composition according to the values given in Table 2 and the 95% confidence interval (equivalent to +/−0.019). Note that in order to determine this value of +/−0.019 the standard deviation is multiplied by the multiplier 1.96 found in the table of Student fractiles. Such a result suggests the existence of flow barriers between the reservoirs represented by these analyses. However, the fluid composition variability in a single reservoir is actually not very well known.

As a result, the maximum threshold value beyond which the presence of a flow barrier between two reservoirs is certain may be greater than zero. The specific implementation method of the process according to this invention explained herein supplies absolute measurements between two footprints. It would therefore be sufficient to set this threshold a single time for a well-known project.

However, by processing the thresholds used on several past projects, a threshold to apply to a new project can be pre-estimated. As knowledge accumulates, it is also possible to determine the expected composition deviations for representatives of a given reservoir based on various parameters such as the distance between sample collection points, the nature of the reservoir rock, fractures, etc.

On a second data set, the distribution analysis result given in Table 3 below for the 95% confidence interval (equivalent to +/−0.015) suggests that the differences between footprints can be entirely attributed to the uncertainty on the peak height measurements. It can be deduced from this that all the samples from this data set come from the same reservoir or are "false negatives." The existence of flow barriers cannot be deduced from differences in composition.

|    | A1     | A2     | B1     | B2    | C1     | C2     | D1     |
|----|--------|--------|--------|-------|--------|--------|--------|
| A2 | −0.001 |        |        |       |        |        |        |
| B1 | −0.013 | −0.014 |        |       |        |        |        |
| B2 | −0.009 | −0.001 | −0.021 |       |        |        |        |
| C1 | 0.005  | 0.011  | −0.001 | 0.006 |        |        |        |
| C2 | 0.004  | 0.018  | −0.003 | 0.006 | −0.003 |        |        |
| D1 | 0.011  | 0.002  | −0.002 | 0.006 | −0.008 | −0.006 |        |
| D2 | 0.001  | 0.008  | 0.002  | 0.002 | −0.013 | −0.016 | −0.005 |

In conclusion, the process according to this invention provides an estimate of peak height ratio uncertainty on the basis of solid theoretical knowledge, even if the number of measurements of each peak height for a given fluid is very limited.

The lesson provided by this invention involves analyzing the distribution of the differences between two representations (in this case, chromatograms) of the same fluid (for example, the same sample), instead of focusing on the values of the peak height ratios associated with those representations. The uncertainty model constructed on two footprints from the same sample (in this case, crude oil) is applied to the other footprints made with the same equipment (in this case, the same chromatograph column), and the number of analyses made for the same data set must be sufficiently restricted to preserve the generality of the model. In the implementation method explained in Example 2 above, each sample results in a pair of analyses supplying pairs of footprints, only one of which was used to construct the uncertainty model.

In addition, the lesson provided by this invention involves determining a deviation between footprints on an absolute scale. The distribution of t variables determined for a pair of analyses is compared to the theoretical distribution obtained if those analyses had come from the same sample. The mean deviation, compared to the expected natural variability, provides an absolute measurement of the differences between these two footprints.

The inventor has determined that these uncertainties between two analyses can be used as a strong basis for estimating the actual deviation between them.

The invention claimed is:

1. A process for determining similarities of signals, comprising:
receiving first and second signals related to material composition, wherein the first and second signals are derived from analyses of two similar samples or an analysis of a single sample;
comparing, by operation of a processor, a first characteristic element of the first signal with a second characteristic element of the second signal to generate a ratio, wherein the first and second characteristic elements are homologous characteristic elements;
determining values for parameters of an uncertainty model using the ratio, a statistical variable based on the ratio, or both;
determining a non-zero composition variation threshold, above which two samples are considered to be derived from two separate sources, using the uncertainty model; and
determining a similarity measurement between at least two other signals derived from two samples, based on each parameter value of the uncertainty model and of homologous characteristic elements in the at least two other signals whose similarity is being measured; and
comparing the similarity measurement with the composition variation threshold to determine whether the at least two other samples are from interconnected or separated sources.

2. The process of claim 1, wherein determining the value comprises optimizing the uncertainty model such that it corresponds to theoretically expected differences between the homologous characteristic elements in the first and second signals.

3. The process of claim 1, wherein determining the value comprises optimizing the uncertainty model such that a distribution of Student variables constructed using the uncertainty model and the ratios corresponds to a theoretical Student distribution with one degree of freedom of differences between the homologous characteristic elements in the signals of similar samples.

4. The process of claim 2, wherein the parameter values minimize a quadratic distance between a theoretical cumulative distribution function and a cumulative distribution function obtained using the homologous characteristic elements of the first and second signals.

5. The process of claim 4, wherein determining the similarity measurement comprises:
calculating differences between the homologous characteristic elements in the at least two other signals whose similarity is being measured; and
determining a mean difference between the homologous characteristic elements of the at least two other signals and a theoretical distribution based on the parameter values.

6. The process of claim 5, wherein the theoretical distribution comprises a theoretical Student distribution based on the parameter values.

7. The process of claim 5, wherein the theoretical distribution comprises a theoretical Gaussian distribution based on the parameter values.

8. The process of any of claims 5 to 7, wherein determining the similarity measurement comprises determining a deviation between the samples based on the mean difference.

9. The process of claim 1, wherein the homologous characteristic elements are homologous peak heights in the first and second signals.

10. The process of claim 1, wherein the homologous characteristic elements are homologous peak height ratios in the first and second signals.

11. The process of claim 1, wherein receiving the first and second signals comprises receiving the first and second signals from a gas chromatograph.

12. The process of claim 1, wherein the uncertainty model is described by:

$$(\sigma_{H_i}^{th})^2 = (\alpha \cdot H_i + \beta)^2$$

in which $\alpha$ and $\beta$ are parameters to be optimized and $H_i$, is the normalized height of peak i.

13. A processing system for determining similarities of signals, comprising:
one or more processors; and
a memory system coupled with the one or more processors, wherein the memory system comprises one or more computer readable media storing instructions that, when executed by the one or more processors, cause the processing system to perform operations, the operations comprising:
receiving first and second signals related to material composition, wherein the first and second signals are derived from analyses of two similar samples or an analysis of a single sample;
comparing, by operation of a processor, a first characteristic element of the first signal with a second characteristic element of the second signal to generate a ratio, wherein the first and second characteristic elements are homologous characteristic elements;
determining values for parameters of an uncertainty model using the ratios, statistical variables based on the ratios, or both;
determining a non-zero composition variation threshold, above which two samples are considered to be derived from two separate sources, using the uncertainty model;
determining a measurement of similarity between at least two other signals derived from two samples, based on the parameter values of the uncertainty module and homologous characteristic elements in the at least two other signals whose similarity is being measured; and comparing the similarity measurement with the composition variation threshold to determine whether the at least two other samples are from interconnected or separated sources.

14. The system of claim 13, further comprising a gas chromatograph configured to provide the first and second signals.

15. The system of claim 13, wherein determining the value comprises optimizing the uncertainty model such that it corresponds to theoretically expected differences between the homologous characteristic elements in the first and second signals.

16. The system of claim 13, wherein determining the value comprises optimizing the uncertainty model such that a distribution of Student variables constructed using the uncertainty model and the ratios corresponds to a theoretical Student distribution with one degree of freedom of differences between the homologous characteristic elements in the signals of similar samples.

17. The system of claim 16, wherein the parameter values minimize a quadratic distance between a theoretical cumulative distribution function and a cumulative distribution function obtained using the homologous characteristic elements of the first and second signals.

18. The system of claim 17, wherein determining the similarity measurement comprises:
calculating differences between the homologous characteristic elements in the at least two other signals whose similarity is being measured; and
determining a mean difference between the homologous characteristic elements of the at least two other signals and a theoretical distribution based on the parameter values.

19. The system of claim 18, wherein the theoretical distribution comprises a theoretical Student distribution based on the parameter values, or a theoretical Gaussian distribution based on the parameter values, or both.

20. The system of claim 16, wherein at least some of the homologous characteristic elements are homologous peak heights or homologous peak height ratios in the first and second signals.

21. The system of claim 16, wherein the uncertainty model is described by:

$$(\sigma_{H_i}^{th})^2 = (\alpha \cdot H_i + \beta)^2$$

in which $\alpha$ and $\beta$ are parameters to be optimized and $H_i$, is the normalized height of peak i.

* * * * *